(12) United States Patent
Mori et al.

(10) Patent No.: US 7,572,578 B2
(45) Date of Patent: *Aug. 11, 2009

(54) METHOD FOR ISOLATING AND PURIFYING A NUCLEIC ACID

(75) Inventors: Toshihiro Mori, Asaka (JP); Yoshihiko Makino, Asaka (JP); Rie Hando, Asaka (JP); Yumiko Takeshita, Asaka (JP); Hiroko Inomata, Asaka (JP)

(73) Assignee: Fujifilm Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/568,101

(22) PCT Filed: Sep. 8, 2004

(86) PCT No.: PCT/JP2004/013384

§ 371 (c)(1),
(2), (4) Date: Feb. 13, 2006

(87) PCT Pub. No.: WO2005/026347

PCT Pub. Date: Mar. 24, 2005

(65) Prior Publication Data

US 2007/0009893 A1 Jan. 11, 2007

(30) Foreign Application Priority Data

| Sep. 9, 2003 | (JP) | ............................. 2003-317104 |
| Sep. 30, 2003 | (JP) | ............................. 2003-339520 |
| Sep. 30, 2003 | (JP) | ............................. 2003-339521 |
| Dec. 24, 2003 | (JP) | ............................. 2003-427355 |
| Mar. 10, 2004 | (JP) | ............................. 2004-066801 |

(51) Int. Cl.
*C12Q 1/68* (2006.01)
(52) U.S. Cl. ....................................... 435/6
(58) Field of Classification Search ............ 435/6
See application file for complete search history.

(56) References Cited

U.S. PATENT DOCUMENTS

| 5,405,951 | A | * | 4/1995 | Woodard ............ 536/25.41 |
| 5,643,721 | A |   | 7/1997 | Spring et al. |
| 5,804,684 | A | * | 9/1998 | Su ........................ 536/25.4 |
| 6,084,091 | A | * | 7/2000 | Muller et al. ............ 536/25.4 |
| 2002/0076823 | A1 | * | 6/2002 | Natrajan et al. ............ 436/172 |
| 2002/0192667 | A1 |   | 12/2002 | Kojima et al. |
| 2003/0078307 | A1 |   | 4/2003 | Shinohara et al. |
| 2003/0170664 | A1 |   | 9/2003 | Mori et al. |
| 2004/0259162 | A1 | * | 12/2004 | Kappel et al. ............. 435/7.1 |
| 2005/0045538 | A1 | * | 3/2005 | Seto et al. ................ 210/143 |
| 2005/0112656 | A1 | * | 5/2005 | Iwaki ........................ 435/6 |

FOREIGN PATENT DOCUMENTS

| JP | 9-508532 A | 9/1997 |
| JP | 2002-348500 A | 12/2002 |
| JP | 2002-348797 A | 12/2002 |
| JP | 2002-360245 A | 12/2002 |
| JP | 2003-38906 A | 2/2003 |
| JP | 2003-128691 A | 5/2003 |
| JP | 2003-144150 A | 5/2003 |
| JP | 2003-506456 A | 12/2003 |
| WO | WO 9708547 | * 3/1997 |
| WO | WO-02/066993 A1 | 8/2002 |

OTHER PUBLICATIONS

Sigma Data Sheet, www.sigmaaldrich.com/sigma/product%20information%20sheet/A6707pis.pdf, pp. 1-3, Dec. 2005.*
Herman Mark, Encyclopedia of Polymer Science and Technology, vol. 1, pp. 670-739, Feb. 2003.*
Su et al., "Cellulose as a Matrix for Nucleic Acid Purification", Analytical Biochemistry, vol. 267, 1999, pp. 415-418.

* cited by examiner

*Primary Examiner*—Gary Benzion
*Assistant Examiner*—Cynthia B Wilder
(74) *Attorney, Agent, or Firm*—Birch, Stewart, Kolasch & Birch, LLP (57) ABSTRACT

The present invention is a method for isolating and purifying a nucleic acid, where generation of foams is able to be suppressed whereby the isolation and purification of a nucleic acid are easily and efficiently carried out, the method for isolating and purifying a nucleic acid comprising the step of: (1) contacting a sample solution containing nucleic acid to a solid phase to adsorb the nucleic acid onto the solid phase; (2) contacting a washing solution to the solid phase to wash the solid phase in such a state that the nucleic acid is adsorbed; and (3) contacting an elution solution to the solid phase to desorb the nucleic acid, wherein the sample solution containing nucleic acid contains an antifoaming agent.

29 Claims, 1 Drawing Sheet

FIG. 1

METHOD FOR ISOLATING AND PURIFYING A NUCLEIC ACID

TECHNICAL FIELD

The present invention relates to a method for isolating and purifying a nucleic acid. More particularly, the present invention relates to a solid phase and a sample solution containing nucleic acid used in a method for isolating and purifying a nucleic acid and also to a method for isolating and purifying a nucleic acid using the same.

BACKGROUND ART

Nucleic acid has been used in various forms in various fields. In the field of recombinant nucleic acid art, for example, it is demanded that nucleic acid is used in forms of probe, genomic nucleic acid and plasmid nucleic acid.

Nucleic acid is used in various forms for various objects in the field of diagnosis as well. For example, nucleic acid probe is routinely used for diagnosis and detection of human pathogen. In addition, nucleic acid is used for detection of genetic disorder and detection of food-polluting substances as well. Further, nucleic acid is routinely used in confirmation of position, identification and isolation of predetermined nucleic acid for various purposes such as preparation of genetic map, cloning and gene expression by genetic recombination.

In many cases however, nucleic acid is available only in a very limited amount and its operation for isolation and purification is troublesome and much time is needed therefor. Such a time-consuming troublesome step has a problem that it is apt to result in loss of nucleic acid. In addition, in the case of purification of nucleic acid from a sample obtained from serum, urine and culture of bacteria, there is a problem that contamination is generated resulting in a pseudo-positive result.

As one of the methods for isolating and purifying a nucleic acid in an easy and efficient manner solving the above-mentioned problems, Japanese Patent Laid-Open No. 2003/128,691 discloses a method using a solution in which nucleic acid is adsorbed with a solid phase and a solution in which nucleic acid is desorbed from the solid phase, in which nucleic acid is adsorbed and desorbed, respectively, with and from the solid phase comprising an organic macromolecule having hydroxyl groups on the surface, whereby nucleic acid is isolated and purified.

DISCLOSURE OF THE INVENTION

However, in conducting the method for isolating and purifying a nucleic acid as such and particularly in using whole blood as a sample, there is a problem that a solution obtained from the sample becomes highly viscous and is apt to generate foams. Further, in adding a surface-active agent for dissolving the cell membrane of the cells in the sample, there is a problem that, in a step of adsorption of nucleic acid with a solid phase, bubbling becomes vigorous as a result of a secondary effect of the surface-active agent. Because of the contamination by scattering of the foams and the influence on the time required for isolating and purifying a nucleic acid, there has been a demand for suppressing the generation of foams.

Accordingly, an object of the present invention is to provide a method for isolating and purifying a nucleic acid, comprising adsorption of nucleic acid onto a solid phase, washing the solid phase under such a state that nucleic acid is adsorbed therewith and desorbing nucleic acid from the solid phase, in which generation of foams in a step of isolating and purifying a nucleic acid is able to be suppressed, or foams generated during the steps are able to be eliminated, whereby isolation and purification of nucleic acid are easily and efficiently carried out. Another object is to provide an apparatus for using the above method for isolating and purifying a nucleic acid and a reagent kit for using the above method for isolating and purifying a nucleic acid.

As a result of their studies, the present inventors have found that, when a sample solution containing nucleic acid contains an antifoaming agent, generation of foams and scattering thereof in conducting the method for isolating and purifying a nucleic acid are able to be significantly suppressed. It has been particularly found in the present invention that, when the sample solution containing nucleic acid contains at least one of silicon type antifoaming agent (antifoaming agent of a silicon type) and alcohol type antifoaming agent (antifoaming agent of an alcohol type), generation of foams and scattering thereof in conducting the method for isolating and purifying a nucleic acid are able to be dramatically suppressed. The present invention has been achieved on the basis of those findings.

Thus, in the present invention, the above-mentioned objects are achieved according to the following constitutions.

1. A method for isolating and purifying a nucleic acid, comprising the step of:
   (1) contacting a sample solution containing nucleic acid to a solid phase to adsorb the nucleic acid onto the solid phase;
   (2) contacting a washing solution to the solid phase to wash the solid phase in such a state that the nucleic acid is adsorbed; and
   (3) contacting an elution solution to the solid phase to desorb the nucleic acid,
   wherein the sample solution containing nucleic acid contains an antifoaming agent.

2. The method for isolating and purifying a nucleic acid according to the item 1, wherein the sample solution containing nucleic acid is prepared by further addition and mixing of a pretreatment solution containing at least one selected from the group consisting of a nucleic acid stabilizer, a chaotropic salt, a surface-active agent, buffer and a protease.

3. The method for isolating and purifying a nucleic acid according to the item 1 or 2, wherein the sample solution containing nucleic acid is prepared by further addition of a water-soluble organic solvent.

4. The method for isolating and purifying a nucleic acid according to any of the items 1 to 3, wherein the antifoaming agent contains at least one of a silicon type antifoaming agent and an alcohol type antifoaming agent.

5. The method for isolating and purifying a nucleic acid according to the item 2, wherein the pretreatment solution contains the nucleic acid stabilizer in a concentration of 0.1 to 20% by mass.

6. The method for isolating and purifying a nucleic acid according to the item 2, wherein the nucleic acid stabilizer is a reducing agent.

7. The method for isolating and purifying a nucleic acid according to the item 6, wherein the reducing agent is a mercapto compound.

8. The method for isolating and purifying a nucleic acid according to the item 2, wherein the nucleic acid stabilizer is a chelating agent.

9. The method for isolating and purifying a nucleic acid according to the item 2, wherein the chaotropic agent is a guanidium salt.

10. The method for isolating and purifying a nucleic acid according to the item 3, wherein the water-soluble organic solvent contains at least one selected from the group consisting of methanol, ethanol, propanol and butanol.

11. The method for isolating and purifying a nucleic acid according to any of the items 1 to 10, wherein the solid phase is a solid phase containing silica or a derivative thereof, diatomaceous earth or alumina.

12. The method for isolating and purifying a nucleic acid according to any of the items 1 to 10, wherein the solid phase is a solid phase containing an organic macromolecule.

13. The method for isolating and purifying a nucleic acid according to the item 12, wherein the organic macromolecule is an organic macromolecule having a polysaccharide structure.

14. The method for isolating and purifying a nucleic acid according to the item 12 or 13, wherein the organic macromolecule is acetylcellulose.

15. The method for isolating and purifying a nucleic acid according to the item 12 or 13, wherein the organic macromolecule is an organic macromolecule where acetylcellulose or a mixture of acetylcelluloses having different acetyl values is subjected to a saponification treatment.

16. The method for isolating and purifying a nucleic acid according to the item 15, wherein degree of saponification of the organic macromolecule prepared by a saponification treatment of the mixture of acetylcelluloses having different acetyl values is 5% or more.

17. The method for isolating and purifying a nucleic acid according to the item 15, wherein degree of saponification of the organic macromolecule prepared by a saponification treatment of the mixture of acetylcelluloses having different acetyl values is 10% or more.

18. The method for isolating and purifying a nucleic acid according to the item 12, wherein the organic macromolecule is a regenerated cellulose.

19. The method according to the items 11 to 18, wherein the solid phase is a porous membrane.

20. The method according to the item 19, wherein the porous membrane is a porous membrane, in which the front and back sides are asymmetric.

21. The method according to the item 19 or 20, wherein the porous membrane is a porous membrane having an average pore diameter of 0.1 to 10.0 μm.

22. The method according to any of the items 19 to 21, wherein the porous membrane is a porous membrane having a thickness of 10 to 500 μm.

23. The method according to any of the items 11 to 18, wherein the solid phase is nonporous.

24. The method according to any of the items 11 to 23, wherein the solid phase is coated beads.

25. The method according to the item 24, wherein the beads are magnetic beads.

26. The method for isolating and purifying a nucleic acid according to any of the items 1 to 25, wherein the adsorption and desorption of nucleic acid are carried out using a cartridge for isolating and purifying a nucleic acid, which houses the solid phase in a container having at least two openings.

27. The method for isolating and purifying a nucleic acid according to any of the items 1 to 26, wherein the adsorption and desorption of nucleic acid are carried out using a unit for isolating and purifying a nucleic acid, which has:
  (a) the solid phase;
  (b) a container having at least two openings, which houses the solid phase; and
  (c) an apparatus for generating the pressure difference, which is connected to one of the openings of the container.

28. The method for isolating and purifying a nucleic acid according to the item 27, wherein the apparatus for generating the pressure difference is an apparatus for pressurization.

29. The method for isolating and purifying a nucleic acid according to the item 27, wherein the apparatus for generating the pressure difference is an apparatus for pressure reduction.

30. The method for isolating and purifying a nucleic acid according to any of the items 27 to 29, wherein the apparatus for generating the pressure difference is connected to one of the openings of the container in a freely detachable manner.

31. The method for isolating and purifying a nucleic acid according to the item 27 or 28, which comprises the step of:
  (2a) preparing a sample solution containing nucleic acid from a sample and infusing the sample solution containing nucleic acid into one of the openings of the container housing the solid phase, the container having at least two openings;
  (2b) making the inner area of the container into a pressurized state by using the apparatus for generating the pressure difference being connected to the one of the openings of the container and contacting the infused sample solution containing nucleic acid to the solid phase by discharging the sample solution from another opening of the container to adsorb nucleic acid onto the solid phase;
  (2c) detaching the apparatus for generating the pressure difference from the one opening of the container and infusing a washing solution into the one opening of the container;
  (2d) making the inner area of the container into a pressurized state by using the apparatus for generating the pressure difference being connected to one of the openings of the container and discharging the infused washing solution from another opening of the container to contact the washing solution to the solid phase to wash the solid phase;
  (2e) detaching the apparatus for generating the pressure difference from the one opening of the container and infusing an elution solution into the one opening of the container; and
  (2f) making the inner area of the container into a pressurized state by using the apparatus for generating the pressure difference being connected to the one of the openings of the container and discharging the infused elution solution from another opening of the container to desorb the adsorbed nucleic acid from the solid phase and discharge nucleic acid outside the container.

32. The method for isolating and purifying a nucleic acid according to the item 31, which comprises, before the step of (2e), (2d') contacting a solution of DNase to the solid phase and then washing the solid phase with the washing solution.

33. The method for isolating and purifying a nucleic acid according to any of the items 1 to 32, wherein the washing solution is a solution containing 20 to 100% by mass of methanol, ethanol, isopropanol or n-propanol.

34. The method for isolating and purifying a nucleic acid according to any of the items 1 to 33, wherein the elution solution is a solution having a salt concentration of not more than 0.5 mol/L.

35. A reagent kit for carrying out the method described in any of the items 1 to 34.

36. An apparatus for carrying out the method described in any of the items 1 to 34.

BEST MODE FOR CARRYING OUT THE INVENTION

The method for isolating and purifying a nucleic acid according to the present invention at least comprises the followings.

(1) A step where a sample solution containing nucleic acid is contacted to a solid phase and nucleic acid is adsorbed with the solid phase (hereinafter, the step may be referred to as "adsorption step"), (2) A step where a washing solution is contacted to the solid phase and the solid phase is washed in such a state that nucleic acid is adsorbed therewith (hereinafter, the step may be referred to as "washing step") and (3) a step where the elution solution is contacted to the solid phase to desorb the nucleic acid (hereinafter, the step may be referred to as "recovering step").

Thus, in the present invention, a sample solution containing nucleic acid is contacted to a solid phase whereby nucleic acid in the sample solution containing nucleic acid is adsorbed onto the solid phase, and washed, and the nucleic acid adsorbed with the solid phase is desorbed from the solid phase using an elution solution.

<Sample Solution Containing Nucleic Acid>

A sample solution containing nucleic acid contains an antifoaming agent. Preferably, it is a solution which is prepared by treating with a pretreatment solution containing at least one member selected from nucleic acid stabilizer, chaotropic salt, surface-active agent, buffer and protease as a reagent for solubilization of nucleic acid and, more preferably, a solution obtained by adding a water-soluble organic solvent thereto.

(Antifoaming Agent)

Examples of the antifoaming agent are an antifoaming agent of a silicon type (such as silicone oil, dimethylpolysiloxane, silicone emulsion, modified polysiloxane and silicone compound), an antifoaming agent of an alcohol type (such as acetylene glycol, heptanol, ethylhexanol, higher alcohol and polyoxyalkylene glycol), an antifoaming agent of an ether type (such as heptyl cellosolve and nonyl cellosolve 3-heptylcorbitol), an antifoaming agent of a fatty acid type (such as stearic acid, oleic acid and palmitic acid), an antifoaming agent of a metal soap type (such as aluminum stearate and calcium stearate), an antifoaming agent of a fatty acid ester type (such as natural wax and tributyl phosphate), an antifoaming agent of a phosphate type (such as sodium octylphosphate), an antifoaming agent of an amine type (such as diamylamine), an antifoaming agent of an amide type (such as stearic amide) and other antifoaming agents (such as ferric sulfate and bauxite) Preferable antifoaming agent is an antifoaming agent of a silicon type or an antifoaming agent of an alcohol type. Those antifoaming agents may be used either solely or jointly. Particularly preferred use is that two components of antifoaming agent of a silicon type and antifoaming agent of an alcohol type are used in combination. With regard to the antifoaming agent of an alcohol type, surface-active agent of an acetylene glycol type is preferred.

The antifoaming agent may be directly added to the sample or may be contained in a pretreatment solution used as a reagent for solubilization of nucleic acid. When the antifoaming agent is not contained in the pretreatment solution, the stage when the antifoaming agent is added may be either before or after the use of the pretreatment solution.

Concentration of the antifoaming agent in a sample solution containing nucleic acid is preferably 0.1 to 10% by mass.

(Sample)

With regard to the sample which is able to be used in the present invention, there is no particular limitation so far as it is a material containing nucleic acid and, in the diagnostic field for example, body fluid such as collected whole blood, plasma, serum, urine, feces, sperm and saliva, or living body material such as plant (or a part thereof), animal (or a part thereof), microbe and virus is an object. It is used as a sample either as it is or as its solution, homogenate or the like.

"Sample" means any sample containing nucleic acid. To be more specific, those which were described in the above sample may be exemplified. Type of the nucleic acid in the sample solution may be either one or more. With regard to the length of each nucleic acid subjected to the above-mentioned method for isolating and purifying a nucleic acid, there is no particular limitation and, for example, it may be a nucleic acid having any length from several bp to several Mbp. In view of handling, it is usually preferred that the length of nucleic acid is from about several bp to several hundred kbp.

In the present invention, "nucleic acid" may be any of single-stranded and double-stranded one and any of DNA and RNA. There is no limitation for the molecular weight thereof as well.

With regard to the sample, it is preferred that cell membrane, nuclear membrane, etc. are dissolved and nucleic acid is dispersed in an aqueous solution to prepare a sample solution containing nucleic acid.

When the sample which is an object is whole blood for example, it is preferred to carry out (A) removal of red blood corpuscles, (B) removal of various proteins and (C) dissolving of white blood corpuscles and dissolving of nuclear membrane. It is preferred that (A) removal of red blood corpuscles and (B) removal of various proteins are conducted for the prevention of non-specific adsorption with the solid phase and of clogging in case porous membrane is used as the solid phase and that (C) dissolving of white blood corpuscles (leucocyte) and dissolving of nuclear membrane is conducted for making nucleic acid which is an object of extraction soluble. Particularly in the method for isolating and purifying a nucleic acid according to the present invention, it is preferred to conduct (C) dissolving of white blood corpuscles and dissolving of nuclear membrane. When the sample is whole blood, it is preferred in the method for isolating and purifying a nucleic acid according to the present invention that nucleic acid is solubilized by conducting those steps.

In the solubilization of nucleic acid by dissolving cell membrane and nuclear membrane in the present invention, it is preferred to use a reagent for solubilization of nucleic acid. It is possible to achieve the above-mentioned (A), (B) and (C) at the same time by, for example, incubating at 60° C. for 10 minutes after addition of guanidine hydrochloride, Triton-X 100 and protease K (manufactured by Sigma).

[Pretreatment Solution]

As mentioned already, with regard to a reagent for solubilization of nucleic acid used in the present invention, it is preferred to use a pretreatment solution containing at least one member selected from nucleic acid stabilizer, chaotropic salt, surface-active agent, buffer and protease. As hereunder, compounds which may be contained in the pretreatment solution will be explained.

(Nucleic Acid Stabilizer)

With regard to a nucleic acid stabilizer, that having an action of inactivating the activity of nuclease may be exemplified. In some samples, nuclease which decomposed nucleic acid or the like may be contained therein and, when nucleic acid is homogenized, the nuclease acts on nucleic acid and the yield may be significantly reduced. The nucleic acid stabilizer is able to make nucleic acid in the test sample stably present and whereby that is preferred.

With regard to a nucleic acid stabilizer having an action of inactivating the nuclease activity, a compound which has been commonly used as a reducing agent may be used. Examples of the reducing agent are hydrogen, hydrogen iodide, hydrogen sulfide, hydride compound such as lithium aluminum hydride and sodium borohydride, highly electrically positive metal such as alkaline metal, magnesium, calcium, aluminum and zinc or amalgam thereof, organic oxide such as aldehyde, saccharide, formic acid and oxalic acid and mercapto compound. Among them, mercapto compound is preferred. Examples of the mercapto compound are N-acetylcysteine, mercaptoethanol and alkyl mercaptan. β-Mercaptoethanol is particularly preferred. The mercapto compound may be used either solely or jointly.

With regard to the nucleic acid stabilizer, its concentration in a pretreatment solution is preferably 0.1 to 20% by mass or, more preferably, 0.3 to 15% by mass. With regard to the mercapto compound, its concentration in the pretreatment solution is preferably 0.1 to 10% by mass or, more preferably, 0.5 to 5% by mass.

It is also possible to use a chelating agent as a nucleic acid stabilizer having an action of stabilizing the nuclear activity. Examples of the chelating agent are ethylenediamine tetraacetic acid (EDTA), nitrilotriacetic acid (NTA) and glycol ether diaminetetraacetic acid (EGTA). The chelating agent may be used either solely or jointly. Concentration of the chelating agent in the pretreatment solution is preferably 1 mmol/L to 1 mol/L or, more preferably, 5 mmol/L to 100 mmol/L.

(Chaotropic Salt)

Examples of a chaotropic salt are guanidine salt, sodium isocyanate, sodium iodide and potassium iodide. Among them, guanidine salt is preferred. Examples of guanidine salt are guanidine hydrochloride, guanidine isothiocyanate and guanidine thiocyanate and, among them, guanidine hydrochloride is preferred. Each of the salts may be used solely or two or more thereof may be used jointly. Concentration of the chaotropic salt in the pretreatment solution is preferably not less than 0.5 mol/L, more preferably 0.5 mol/L to 4 mol/L or, still more preferably, 1 mol/L to 3 mol/L.

Instead of a chaotropic salt, it is also possible to use urea as a chaotropic substance.

(Surface-Active Agent)

Examples of a surface-active agent are nonionic surface-active agent, cationic surface-active agent, anionic surface-active agent and amphoteric surface-active agent.

In the present invention, nonionic surface-active agent and cationic surface-active agent are preferably used.

Examples of the nonionic surface-active agent are surface-active agent of a polyoxyethylene alkyl phenyl ether type, surface-active agent of a polyoxyethylene alkyl ether type and fatty acid alkanol amide and surface-active agent of a polyoxyethylene alkyl ether type is preferred. Among the surface-active agent of a polyoxyethylene alkyl ether type, more preferred ones are POE decyl ether, POE lauryl ether, POE tridecyl ether, POE alkylene decyl ether, POE sorbitan monolaurate, POE sorbitan monooleate, POE sorbitan monostearate, polyoxyethylene sorbitol tetraoleate, POE alkylamine and POE acetylene glycol.

Examples of the cationic surface-active agent are cetyltrimethylammonium bromide, dodecyltrimethylammonium chloride, tetradecyltrimethylammonium chloride and cetylpyridinum chloride.

Each of those surface-active agents may be used solely or two or more thereof may be used jointly. Concentration of the surface-active agent in the above pretreatment solution is preferably 0.1 to 20% by mass.

(Buffer)

Examples of the buffer are the commonly used pH buffers. Preferred examples are pH buffers which are commonly used for biochemical tests. Examples of such buffers are buffer comprising citrate, phosphate or acetate, Tris-HCl, TE (Tris-HCl/EDTA), TBe (Tris-borate/EDTA), TAE (Tris-acetate/EDTA) and Good's buffer. Examples of a Good's buffer are MES (2-morpholinoethanesulfonic acid), Bis-Tris (bis(2-hydroxyethyl)iminotris(hydroxymethyl)methane), HEPES (2-[4-(2-hydroxyethyl)-1-piperazinyl]ethanesulfonic acid), PIPES (piperaxine-1,4-bis (2-ethanesulfonic acid), ACES (N-(2-acetamino)-2-aminoethanesulfonic acid) and TES (N-tris(hydroxymethyl)methyl-2-aminoethanesulfonic acid).

Concentration of the buffer in the above pretreatment solution is preferably 1 to 300 mmol/L.

(Protease)

Examples of protease are serine protease, cysteine protease and metal protease and at least one protease may be used preferably. In addition, with regard to protease, a mixture of two or more proteases may be preferably used as well.

In view of improvement in recovering amount and recovering efficiency of nucleic acid and in view of making a sample containing necessary nucleic acid finely small and quick, it is preferred that the pretreatment solution contains protease.

With regard to serine protease, there is no particular limitation and, for example, Protease K may be used preferably. With regard to cysteine protease, there is no particular limitation and, for example, papain and cathepsin may be used preferably. With regard to metal protease, there is no particular limitation and, for example, carboxypeptidase may be used preferably.

Concentration of the protease in the above pretreatment solution per 1 ml of total volume upon addition is preferably 0.01 IU to 10 IU or, more preferably, 0.01 IU to 1 IU.

With regard to the protease, a protease containing no enzyme which decomposes nucleic acid is preferably used. A protease containing a stabilizer may be preferably used as well. With regard to the stabilizer, metal ion may be preferably used. To be more specific, magnesium ion is preferred and, for example, it may be added in a form of magnesium chloride. When a stabilizer for protease is contained therein, it is possible that protease necessary for recovery of nucleic acid is made finely small whereby the cost necessary for the recovery of nucleic acid is able to be reduced.

Concentration of a stabilizer for protease in the above pretreatment solution is preferably 0 to 1,000 mmol/L or, more preferably, 10 to 100 mmol/L.

Protease may be subjected to recovery of nucleic acid as a pretreatment solution (hereinafter, referred to as a pretreatment solution A) by mixing with a reagent such as chaotropic salt, surface-active agent and buffer previously.

Protease may also be subjected to the use as two or more reagents being separate from a pretreatment solution (hereinafter, referred to as pretreatment solution B) containing chaotropic salt, surface-active agent, buffer and other reagents. In the latter case, a reagent containing protease is firstly mixed with a sample and then mixed with a pretreatment solution B. It is also possible that a pretreatment solution B is firstly mixed with a sample and then mixed with protease.

It is further possible that protease is directly dropped, as if eye drop, from a container in which protease is stored into a sample or a mixed solution of a sample with a pretreatment solution B. In that case, operation is able to be made easy.

It is also preferred that the pretreatment solution is supplied in a dry state or, in other words, as a pretreatment agent. It is further possible to use a container in which protease in a dry state such as being freeze-dried is previously contained. It is still further possible to prepare a sample solution containing nucleic acid using the above-mentioned container in which the pretreatment agent and/or protease in a dry state are/is previously contained.

In preparing a sample solution containing nucleic acid by the above-mentioned method, stability of the pretreatment agent and protease in a dry state upon storage is good and an operation is able to be made easy without changing the yield of nucleic acid.

A water-soluble organic solvent may also be added to the pretreatment solution in view of enhancement of solibility of the above-mentioned compounds contained in the sample solution. Examples of the water-soluble organic solvent are alcohols, acetone, acetonitrile and dimethylformamide. Among them, alcohols are preferred in view of improvement in solubility of the above-mentioned compound contained in a sample solution. With regard to the alcohols, any of primary, secondary and tertiary alcohols may be used. Specific examples are methanol, ethanol, propanol and an isomer thereof and butanol and isomers thereof and, among them, ethanol is particularly preferred. Each of those water-soluble organic solvents may be used solely or two or more thereof may be used jointly. It is preferred to prepare so as to make concentration of the above water-soluble organic solvent 1 to 20% by mass in a sample solution containing nucleic acid.

[Water-Soluble Organic Solvent and Adsorption Step]

In order to effectively adsorb nucleic acid in the sample solution onto the solid phase by adding a water-soluble organic solvent to a solution in which nucleic acid is solubilized and dispersed and contacting the solid phase, a sample solution containing nucleic acid is preferred to be a solution to which a water-soluble organic solvent is further added. Thus, it is preferred that a water-soluble organic solvent is further added to a solution prepared by addition of an antifoaming agent to the above sample or to a solution prepared by treating with a pretreatment solution, whereby a sample solution containing nucleic acid is prepared. When a water-soluble organic solvent is added to a solution in which nucleic acid is dissolved and dispersed to prepare a sample solution containing nucleic acid and to contact to a solid phase, nucleic acid in the sample solution is effectively adsorbed with the solid phase and, therefore, that is preferred. Further, when a salt is present in the resulting sample solution containing nucleic acid, the solubilized nucleic acid is able to be more effectively adsorbed with the solid phase and, therefore, that is preferred.

Due to the presence of a water-soluble organic solvent and a salt, hydrated structure of water molecules existing around nucleic acid is destroyed and nucleic acid is solubilized in an unstable state. It is believed that, when nucleic acid under such a state is contacted to a solid phase, an interaction takes place between polar groups on the surface of nucleic acid and polar groups on the surface of solid phase whereby nucleic acid is adsorbed with the surface of the solid phase. Especially when an organic macromolecule having hydroxyl groups on the surface is used as a solid phase, significant adsorption takes place and that is preferred. As mentioned above, according to the present invention, nucleic acid is able to be made into an unstable state by the fact that a water-soluble organic solvent is mixed with a solution of mixed solubilized nucleic acid solution and that a salt is present in the resulting solution of mixed nucleic acid whereby that is preferred.

Examples of the water-soluble organic solvent are alcohol, acetone, acetonitrile and dimethylformamide. Among them, alcohol is preferred. With regard to the alcohol, any of primary, secondary and tertiary alcohols may be used. Among them, methanol, ethanol, propanol and isomer thereof and butanol and isomers thereof may be preferably used. Ethanol is used more preferably. Each of those water-soluble organic solvent may be used solely or two or more thereof may be used jointly.

It is preferred that the final concentration of such a water-soluble organic solvent in a sample solution containing nucleic acid is 5 to 90% by mass. With regard to the concentration of ethanol added thereto, it is particularly preferred to be as high as possible within the above range so far as no aggregate is produced. It is more preferred to be 20% by mass to 60% by mass.

Examples of the salt which is preferred to be present in the resulting nucleic acid mixed solution are various chaotropic substances (such as guanidium salt, sodium iodide and sodium perchlorate), sodium chloride, potassium chloride, ammonium chloride, sodium bromide, potassium bromide, calcium bromide and ammonium bromide. Guanidium salt is particularly preferred since it has both effects of solubilization of cell membrane and solubilization of nucleic acid.

With regard to pH of the resulting sample solution, it is preferred to use the solution of pH 3 to 10, more preferably pH 4 to 9 and, still more preferably, pH 5 to 8.

With regard to the resulting sample solution containing nucleic acid, it is preferred that surface tension is not more than 0.05 J/m$^2$, viscosity is 1 to 10,000 mPa and specific gravity is within a range of 0.8 to 1.2. When a solution within such a range is prepared, a solution which remains after a process where a sample solution containing nucleic acid is contacted to the above solid phase in an adsorption step to adsorb nucleic acid is able to be easily removed in a washing step.

<Solid Phase and Adsorption Step>

With regard to a solid phase, there is no particular limitation and any material may be used so far as it is able to adsorb nucleic acid. For example, a solid phase comprising an organic macromolecule having hydroxyl group on the surface, a solid phase comprising silicon dioxide, silica polymer or magnesium silicate or a solid phase comprising silica or derivative thereof, diatomaceous earth or alumina may be used. It is preferred to use a solid phase comprising an organic macromolecule having a polysaccharide structure. It is more preferred to use a solid phase where nucleic acid is adsorbed therewith by an interaction in which ionic bond is not substantially participated. The above means it is not "ionized" under the condition for using the solid phase and it is presumed that, when polarity of environment is changed, nucleic acid and solid phase pull against each other. As a result thereof, nucleic acid is able to be isolated and purified with a good separating efficiency and with a good washing efficiency. An example of a solid phase where nucleic acid is adsorbed therewith by an interaction in which ionic bond is not substantially participated, for example, is a solid phase having hydrophilic groups and it is presumed that, when polarity is changed, hydrophilic groups of nucleic acid and solid phase pull each other.

Hydrophilic group means a polar group (atomic group) which is able to interact with water and all groups (atomic groups) participating in adsorption of nucleic acid are covered therein. With regard to a hydrophilic group, its action with water is in a medium degree (refer to "Groups having not so strong hydrophilicity" under the item of "Hydrophilic groups" in "*Kagaku Daijiten*" (Encyclopedia Chimica) published by Kyoritsu Shuppan K. K.) is recommended and its examples are hydroxyl group, carboxy group, cyano group and oxyethylene group. A preferred example is hydroxyl group.

A solid phase having hydrophilic groups means that the material itself forming the solid phase has hydroxyl groups or it means a solid phase into which hydrophilic groups are introduced by treating or coating of a material forming the solid phase. The material forming the solid phase may be any of organic and inorganic substances. Examples of the solid phase which is able to be used are a solid phase where the material itself forming the solid phase is an organic material having hydrophilic groups, a solid phase where a solid phase of an organic material having no hydrophilic group is treated so as to introduce hydrophilic groups thereinto, a solid phase where a solid phase of an organic material having no hydrophilic group is coated with a material having hydrophilic groups so as to introduce hydrophilic groups thereinto, a solid phase where a material itself forming the solid phase is an inorganic material having hydrophilic group, a solid phase where the solid phase of an inorganic material having no hydrophilic group is treated so as to introduce hydrophilic groups thereinto and a solid phase where a solid phase of inorganic material having no hydrophilic group is coated with a material having hydrophilic groups so as to introduce hydrophilic groups thereinto. Among them, it is preferred in view of easiness in processing to use an organic material such as organic macromolecule as a material for forming a solid phase.

[Organic Material Having Hydrophilic Groups]

With regard to an organic material having hydrophilic groups, an organic material having hydroxyl group may be exemplified. Examples of the organic material having hydroxyl group are polyhydroxyethyl acrylic acid, polyhydroxyethyl methacrylic acid, polyvinyl alcohol, polyvinylpyrrolidone, polyacrylic acid, polymethacrylic acid, polyoxyethylene and organic material having a polysaccharide structure (may also be called organic macromolecule having a polysaccharide structure).

Examples of the organic material having a polysaccharide structure are cellulose, hemicellulose, dextrin, agarose, dextrin, amylose, amylopectin, starch, glycogen, pullulan, mannan, glucomannan, lichenan, isolichenan, carrageenan, xylan, fructan, alginic acid, hyaluronic acid, chondroitin, chitin and chitosan. It is also possible to use derivatives of such polysaccharide structures and examples thereof are those wherein hydroxyl groups of the polysaccharide structure are esterified, etherified or halogenated in any degree of substitution. It is possible to use without being limited to the above-mentioned materials so far as the material is at least any of the polysaccharide and derivative thereof. Those derivatives may be produced by the methods which have been known up to now.

Ester derivative is particularly preferably used. Saponified products of ester derivative may also be exemplified as suitable ones.

Examples of the ester in the above-mentioned ester derivatives of polysaccharide structure are carboxylate, nitrate, sulfate, sulphonate, phosphate, phosphonate and pyrophosphate and it is preferred that the ester derivative is at least one member selected from those esters. Saponified products of ester derivative may also be exemplified as suitable ones.

Examples of the above carboxylate are alkylcarbonyl ester, alkenylcarbonyl ester, aromatic carbonyl ester and aromatic alkylcarbonyl ester and, when carboxylate is used as an ester, it is preferred to be at least one member selected from those carboxylates. Saponified products of those carboxylates may also be exemplified as suitable ones.

Examples of the alkylcarbonyl group of the above alkylcarbonyl ester are acetyl group, propionyl group, butyroyl group, valeryl group, heptanoyl group, octanoyl group, decanoyl group, dodecanoyl group, tridecanoyl group, hexadecanoyl group and octadecanoyl group and, when an alkylcarbonyl ester is used as a carboxylate, it is preferred to have at least one member selected from those alkylcarbonyl groups. Saponified products of those alkylcarbonyl esters may also be exemplified as suitable ones.

Examples of the alkenylcarbonyl group of the above alkenylcarbonyl ester are acryl group and methacryl group and, when an alkenylcarbonyl ester is used as a carboxylate, it is preferred to have at least one member selected from those alkenylcarbonyl groups. Saponified products of those alkenylcarbonyl esters may also be exemplified as suitable ones.

Examples of an aromatic carbonyl group in the above aromatic carbonyl esters are benzoyl group and naphthaloyl group and, when an aromatic carbonyl ester is used as a carboxylate, it is preferred to have at least one member selected from those aromatic carbonyl esters. Saponified products of those aromatic carbonyl esters may also be exemplified as suitable ones.

Examples of the above nitrate are nitrocellulose, nitrohemicellulose, nitrodextran, nitroagarose, nitrodextrin, nitroamylose, nitroamylopectin, nitroglycogen, nitropullulan, nitromannan, nitroglucomannan, nitrolichenan, nitroisolichenan, nitrolaminaran, nitrocarrageenan, nitroxylan, nitrofructan, nitroalginic acid, nitrohyaluronic acid, nitrochondroitin, nitrochitin and nitrochitosan. Saponified products of those nitrates may also be exemplified as suitable ones.

Examples of the above sulfate are cellulose sulfate, hemicellulose sulfate, dextran sulfate, agarose sulfate, dextrin sulfate, amylose sulfate, amylopectin sulfate, glycogen sulfate, pullulan sulfate, mannan sulfate, glucomannan sulfate, lichenan sulfate, isolichenan sulfate, laminarin sulfate, carrageenan sulfate, xylan sulfate, fructan sulfate, alginic acid sulfate, hyaluronic acid sulfate, chondroitin sulfate, chitin sulfate and chitosan sulfate. Saponified products of those sulfates may also be exemplified as suitable ones.

Examples of the above sulfonate are alkyl sulfonate, alkenyl sulfonate, aromatic sulfonate and aromatic alkyl sufonate and, when sulfonate is used as an ester, it is preferred to be at least one member selected from those sulfonates. Saponified products of those sulfonates may also be exemplified as suitable ones.

Examples of the above phosphate are cellulose phosphate, hemicellulose phosphate, dextran phosphate, agarose phosphate, dextrin phosphate, amylose phosphate, amylopectin phosphate, glycogen phosphate, pullulan phosphate, mannan phosphate, glucomannan phosphate, lichenan phosphate, isolichenan phosphate, laminarin phosphate, carrageenan phosphate, xylan phosphate, fructan phosphate, alginic acid phosphate, hyaluronic acid phosphate, chondroitin phosphate, chitin phosphate and chitosan phosphate. Saponified products of those phosphates may also be exemplified as suitable ones.

Examples of the above phosphonate are cellulose phosphonate, hemicellulose phosphonate, dextran phosphonate, agarose phosphonate, dextrin phosphonate, amylose phosphonate, amylopectin phosphonate, glycogen phosphonate, pullulan phosphonate, mannan phosphonate, glucomannan phosphonate, lichenan phosphonate, isolichenan phosphonate, laminarin phosphonate, carrageenan phosphonate, xylan phosphonate, fructan phosphonate, alginic acid phosphonate, hyaluronic acid phosphonate, chondroitin phosphonate, chitin phosphonate and chitosan phosphonate. Saponified products of those phosphonates may also be exemplified as suitable ones.

Examples of the above pyrophosphate are cellulose pyrophosphate, hemicellulose pyrophosphate, dextran pyrophosphate, agarose pyrophosphate, dextrin pyrophosphate, amylose pyrophosphate, amylopectin pyrophosphate, glycogen pyrophosphate, pullulan pyrophosphate, mannan pyrophosphate, glucomannan pyrophosphate, lichenan pyrophosphate, isolichenan pyrophosphate, laminarin pyrophosphate, carrageenan pyrophosphate, xylan pyrophosphate, fructan pyrophosphate, alginic acid pyrophosphate, hyaluronic acid pyrophosphate, chondroitin pyrophosphate, chitin pyrophosphate and chitosan pyrophosphate. Saponified products of those pyrophosphates may also be exemplified as suitable ones.

With regard to an ether in an ether derivative of the above polysaccharide structure, examples of the ether when the polysaccharide structure is cellulose are mentioned below although they are not limited to them only including the type of polysaccharide structure and the type of ether.

Examples are methylcellulose, ethylcellulose, carboxymethylcellulose, carboxyethylcellulose, carboxyethyl-carbamoylethyl cellulose, hydroxymethylcellulose, hydroxyethylcellulose, hydroxypropylcellulose, hydroxypropylmethyl cellulose, hydroxyethylmethyl cellulose, cyanoethylcellulose and carbamoylethylcellulose. Preferred ones are hydroxymethylcellulose and hydroxyethylcellulose.

With regard to an organic material having a polysaccharide structure, acetylcellulose is preferably exemplified and a mixture of acetylcelluloses having different acetyl values is further exemplified. With regard to a mixture of acetylcelluloses having different acetyl values, a mixture of triacetylcellulose and diacetylcellulose, a mixture of triacetylcellulose and monoacetylcellulose, a mixture of triacetylcellulose, diacetylcellulose and monoacetylcellulose and a mixture of diacetylcellulose and monoacetylcelluose may be preferably used.

A mixture of triacetylcellulose and diacetylcellulose is particularly preferred. Mixing ratio (ratio by mass) of triacetylcelluose to diacetylcellulose is preferably 99:1 to 1:99 and, more preferably, 90:10 to 50:50.

Among the acetylcellulose which is preferably used as an organic material having a polysaccharide structure, a surface saponified product of acetylcellulose mentioned in Japanese Patent Laid-Open No. 2003/128,691 is particularly preferred. With regard to the surface saponified product of acetylcellulose (hereinafter, it will be sometimes referred to just "saponified product"), a product where an acetylcellulose mixture having different acetyl values is subjected to a saponifying treatment and a saponified product of a mixture of triacetylcellulose and diacetylcellulose, a saponified product of a mixture of triacetylcellulose, diacetylcellulose and monoacetylcellulose and a saponified product of a mixture of diacetylcellulose and monoacetylcellulose may be preferably used. It is more preferred to use a saponified product of a mixture of triacetylcellulose and diacetylcellulose and their mixing ratio (ratio by mass) is within the same range as that mentioned already for a mixture of acetylcelluloses having different acetyl values. It is possible to control the amount (density) of hydroxyl groups on the solid phase surface by way of degree of the saponifying treatment (degree of saponification) and that is preferred. In view of improvement in efficiency of separation of nucleic acid, the more the amount (density) of hydroxyl groups, the better. It is preferred that degree of saponification (degree of surface saponification) of the solid phase prepared by the saponifying treatment is from 5% to 100% and it is more preferred to be from 10% to 100%.

In addition, in view of making the surface area having hydroxyl group in the solid phase large, it is preferred that acetylcellulose is subjected to a saponifying treatment to give a solid phase.

In order to prepare the above-mentioned saponified product, a saponifying treatment is carried out. Here, the saponifying treatment means that an organic material having ester group is contacted to a saponifying treatment solution (such as an aqueous solution of sodium hydroxide). As a result thereof, the are a contacting to the saponifying treatment solution or, in other words, surface of the organic material is saponified. In the case of acetylcellulose, the area contacting to the saponifying treatment solution becomes a regenerated cellulose into which hydroxyl groups are introduced. The regenerated cellulose prepared as such is different from the starting cellulose in terms of crystalline state, etc. In the present invention, it is particularly preferred to use a solid phase containing a regenerated cellulose as a solid phase.

In changing the degree of saponification, a saponifying treatment is carried out by changing the concentration of sodium hydroxide. Degree of saponification is able to be easily measured by means of NMR (for example, it is able to be determined by the degree of reduction of peak of carbonyl group).

[Organic Material Having No Hydrophilic Group]

As a method for introduction of hydrophilic group into an organic material when an organic material having no hydrophilic group is used as a solid phase, a graft polymer chain having hydrophilic groups in a polymer chain or on a side chain may be bonded to the organic material.

With regard to a method for bonding a graft polymer chain to an organic material, there are two methods where one is a method of subjecting an organic material and a graft polymer chain to chemical bonding and another is a method of polymerizing a compound having polymerizable double bond using an organic material as a starting point to prepare a graft polymer chain.

Firstly, in a method where an organic material and a graft polymer chain are subjected to chemical bonding, a polymer having a functional group reacting with an organic material at the end or the side chain of the polymer is used and the functional group is subjected to chemical bonding to a functional group of an organic material to graft. With regard to a functional group reacting with an organic material, there is no particular limitation so far as it is able to react with a functional group of the organic material and its examples are silane coupling group such as alkoxysilane, isocyanate group, amino group, hydroxyl group, carboxy group, sulfonic acid group, phosphoric acid group, epoxy group, allyl group, methacryloyl group and acryloyl group.

Examples of a compound which is particularly important as a polymer having a reactive functional group at the end or the side chain of a polymer are polymer having a trialkoxysilyl group at the end of the polymer, polymer having an amino group at the end of the polymer, polymer having a carboxy group at the end of the polymer, polymer having an epoxy group at the end of the polymer and polymer having an isocyanate group at the end of the polymer. With regard to the polymer used therefor, there is no particular limitation so far as it has a hydrophilic group participating in adsorption of nucleic acid and specific examples thereof are polyhydroxyethyl acrylic acid, polyhydroxyethyl methacrylic acid and salts thereof, polyvinyl alcohol, polyvinylpyrrolidone, polyacrylic acid, polymethacrylic acid and salts thereof and polyoxyethylene.

A method where a compound having a polymerizable double bond is polymerized using an organic material as a starting point to give a graft polymer chain is usually called a surface graft polymerization. A surface graft polymerization stands for a method where active species are given on the surface of an organic material by means of irradiation of plasma, irradiation of light, heating, etc. and a compound having a polymerizable double bond aligned to make adjacent to an organic material is bonded to an organic material by polymerization.

It is necessary that a compound which is useful for forming a graft polymer chain bonding to an organic material has both of the two characteristics that it has a polymerizable double bond and that it has a hydrophilic group participating in adsorption of nucleic acid. With regard to the compound as such, any of polymer, oligomer and monomer having a hydrophilic group may be used so far as it has a double bond in a molecule. Particularly useful compound is a monomer having a hydrophilic group.

Specific examples of the particularly useful monomer having a hydrophilic group are monomers having a hydroxyl group such as 2-hydroxyethyl acrylate, 2-hydroxyethyl methacrylate and glycerol monomethacrylate. A monomer containing carboxy group such as acrylic acid and methacrylic acid or alkaline metal salt and amine salt thereof may be also used preferably.

As to another method for introduction of hydrophilic group into an organic material having no hydrophilic group, a method where a material having a hydrophilic group is coated may be used. There is no particular limitation for a material used for the coating so far as it has a hydrophilic group participating in adsorption of nucleic acid and, in view of easiness of operation, polymer of an organic material is preferred. Examples of the polymer are polyhydroxyethyl acrylic acid, polyhydroxyethyl methacrylic acid and salts thereof, polyvinyl alcohol, polyvinylpyrrolidone, polyacrylic acid, polymethacrylic acid and salts thereof, polyoxyethylene, acetylcellulose and a mixture of acetylcelluloses having different acetyl values and the polymer having a polysaccharide structure is preferred.

It is also possible that an organic material having no hydrophilic group is coated with acetylcellulose or a mixture of acetylcelluloses having different acetyl values and then the coated acetylcellulose or a mixture of acetylcelluloses having different acetyl values is subjected to a saponifying treatment. In that case, it is preferred that degree of saponification is from 5% to 100%. It is more preferred that degree of saponification is from 10% to 100%.

[Inorganic Material Having Hydrophilic Group]

With regard to an inorganic material having no hydrophilic group, a silica compound may be exemplified. With regard to a solid phase containing a silica compound, glass filter may be exemplified. Porous thin membrane of silica as mentioned in Japanese Patent No. 3,058,342 may be also exemplified. The porous thin membrane of silica may be prepared in such a manner that a developing solution of amphipathic substance of a cation type having an ability of formation of bimolecular membrane is developed on a substrate, the solvent is removed from liquid membrane on the substrate to prepare a multi-layered bimolecular thin membrane of the amphipathic substance, a multi-layered bimolecular thing membrane is contacted to a solution containing a silica compound and then the above-mentioned multi-layered bimolecular thin membrane is extracted and removed.

[Inorganic Material Having No Hydrophilic Group]

Examples of an inorganic material having no hydrophilic group being able to be used as a solid phase are metal such as aluminum, ceramic such as glass, cement and pottery, new ceramics, silicon and active charcoal.

With regard to a method for introduction of hydrophilic groups into an inorganic material having no hydrophilic group, there are two methods. One is a method where an inorganic material and graft polymer chain having hydrophilic group are subjected to a chemical bonding and another is a method where graft polymer chain is polymerized using a monomer having a double bond in a molecule and having a hydrophilic group in which an inorganic material is a starting point.

When an inorganic material and graft polymer having hydrophilic group are subjected to a chemical bonding, a functional group which reacts with a functional group at the end of a graft polymer chain is introduced into an inorganic material and a graft polymer is chemically bonded thereto. In the case where graft polymer chain is polymerized using a monomer having a double bond in a molecule and having a hydrophilic group in which an inorganic material is a starting point, a functional group which is a starting point upon polymerization of a compound having a double bond is introduced into an inorganic material.

With regard to a graft polymer having hydrophilic group and a monomer having a double in a molecule and having hydrophilic group, a graft polymer having hydrophilic group and a monomer having a double in a molecule and having hydrophilic group which are mentioned in the above method for introduction of hydrophilic group into an organic material having no hydrophilic group may be preferably used.

As to another method for introduction of hydrophilic group into an inorganic material having no hydrophilic group, a material having a hydrophilic group may be coated. There is no particular limitation for a material used for the coating so far as it has a hydrophilic group participating in adsorption of nucleic acid and, in view of easiness of operation, polymer of an organic material is preferred. Examples of the polymer are polyhydroxyethyl acrylic acid, polyhydroxyethyl methacrylic acid and salts thereof, polyvinyl alcohol, polyvinylpyrrolidone, polyacrylic acid, polymethacrylic acid and salts thereof, polyoxyethylene, acetylcellulose and a mixture of acetylcelluloses having different acetyl values and the polymer having a polysaccharide structure is preferred.

It is also possible that an inorganic material having no hydrophilic group is coated with acetylcellulose or a mixture of acetylcelluloses having different acetyl values and then the coated acetylcellulose or a mixture of acetylcelluloses having different acetyl values is subjected to a saponifying treatment. In that case, it is preferred that degree of saponification is from 5% to 100%. It is more preferred that degree of saponification is from 10% to 100%.

[Properties]

The above-mentioned solid phase may be in any shape so far as solution is able to contact thereto. For example, a shape where solution contacts to the surface such as that the solid phase is fiber or, as will be mentioned later, a shape where a solution is able to pass through the inside may be adopted.

Further, beads may be used as a solid phase after coating with the above-mentioned material. It is preferred that the beads are coated with a mixture of acetylcelluloses having different acetyl values. In that case, magnetic beads may be used as the beads. For example, membrane of triacetylcellulose may be formed on the surface of beads made of polyethylene. Thus, triacetylcellulose is coated on the beads. Material for the beads is not limited to polyethylene but may be anything so far as it does not, for example, pollute nucleic acid.

It is preferred that solid phase is used in a shape of filter or membrane where a solution is able to pass through the inside (hereinafter, it may be referred to a solid phase where a solution is able to pass the inside). In that case, it is preferred that its thickness is 10 μm to 500 μm. More preferably, the thickness is 50 μm to 250 μm. The fact of within such a range is preferred in view of washing.

The above-mentioned solid phase where a solution is able to pass through the inside is preferred to be a porous membrane and an average pore size is preferred to be 0.1 μm to 10 μm. More preferably, the average pore size is 1 μm to 5 μm. Within such a range, a sufficient surface area for adsorption of nucleic acid is achieved and clogging hardly takes place whereby that is preferred. Average pore size of the solid phase where a solution is able to pass through the inside is able to be determined by a bubble point method (cf. ASTM F316-86, JIS K-3832).

The above-mentioned solid phase where a solution is able to pass through the inside may be a porous membrane where front and back are symmetric. It is also possible that front and back are asymmetric. The expression that front and back are asymmetric means a property that physical property or chemical property of the membrane changes from one surface to another surface of the porous membrane.

An example of the physical property of a membrane is average pore size. An example of the chemical property of a membrane is degree of saponification.

When a porous membrane where average pore size is asymmetric for front and back is used in the present invention, it is preferred to use in such a manner that average pore size varies from big to small in the passing direction of the solution. Here, it is preferred to use a porous membrane where the ratio of maximum pore size to minimum pore size is 2 or more. More preferably, the ratio of maximum pore size to minimum pore size is 5 or more. Within such a range, a sufficient surface area for adsorption of nucleic acid is achieved and clogging hardly takes place whereby that is preferred.

In the above-mentioned solid phase where a solution is able to pass through the inside, it is preferred that its void fraction is 50 to 90%. More preferably, the void fraction is 65 to 80%. In addition, it is preferred that a bubble point is 0.1 to 10 $kgf/cm^2$. More preferably, the bubble point is 0.2 to 4 $kgf/cm^2$.

In the above-mentioned solid phase where a solution is able to pass through the inside, it is preferred that its pressure drop is 0.1 to 100 kPa. Within such a range, a uniform pressure is achieved during overpressure and that is preferred. More preferably, the pressure drop is 0.5 to 50 kPa. Here, a pressure drop means a minimum pressure necessary for passing water per 100 μm thickness of the membrane.

In the above-mentioned solid phase where a solution is able to pass through the inside, it is preferred that permeated water amount when water is passed at 25° C. under the pressure of 1 $kg/cm^2$ is 1 to 5,000 mL per minute per 1 $cm^2$ of the membrane. More preferably, the permeated water amount when water is passed at 25° C. under the pressure of 1 $kg/cm^2$ is 5 to 1,000 mL per minute per 1 $cm^2$ of the membrane.

In the above-mentioned solid phase where a solution is able to pass through the inside, it is preferred that adsorbed amount of nucleic acid per 1 mg of the porous membrane is 0.1 μg or more. More preferably, the adsorbed amount of nucleic acid per 1 mg of the porous membrane is 0.9 μg or more.

It is preferred that flow rate for contacting a sample solution containing nucleic acid through the above-mentioned solid phase is 2 to 1,500 μL/sec per 1 $cm^2$ of the area of the solid phase for achieving an adequate contacting time of the solution to the solid phase. When the contacting time of the solution to the solid phase is too short, a sufficient separation and purification effect is not achieved while, when it is too long, that is not preferred in view of operability. Further, it is preferred that the above-mentioned flow rate is 5 to 700 μL/sec per 1 $cm^2$ of the area of the solid phase.

With regard to the solid phase where a solution is able to pass through the inside, only one may be used or plural ones may be used. Solid phases in plural may be either in the same material or in difference ones.

<Washing Step>

A washing step will be illustrated as hereunder. When nucleic acid is adsorbed with a solid phase and then the solid phase is washed, recovered amount and purity of nucleic acid are improved whereby the necessary amount of the sample containing nucleic acid is able to be made very small. When the washing step and a recovering step which will be mentioned later are automated, it is now possible to conduct the operations easily and quickly and that is preferred. With regard to the washing step, that may be conducted only once for making the step quick but, when purity is more important, it is preferred to repeat the washing for plural times.

It is preferred that the washing solution is a solution containing a water-soluble organic solvent and/or a water-soluble salt. If necessary, buffer and surface-active agent may be also contained therein. It is necessary that the washing solution has a function of washing out impurities in the sample solution which is adsorbed with the solid phase together with nucleic acid. For such a purpose, the composition is to be in such a manner that nucleic acid is not desorbed from the solid phase while impurities are able to be desorbed therefrom. For such a purpose, nucleic acid is hardly soluble in a water-soluble organic solvent such as alcohol and, therefore, that is appropriate for desorbing the components other than nucleic acid where nucleic acid still retained. Since adsorbing effect for nucleic acid is enhanced when a water-soluble salt is added, a selective removing action for impurities and unnecessary component is enhanced and that is preferred.

With regard to the water-soluble organic solvent contained in a washing solution, alcohol, acetone, etc. may be used and alcohol is preferred. Examples of alcohol are methanol, ethanol, propanol and butanol. With regard to propanol, it may be any of isopropanol and n-propanol and, with regard to butanol, it may be either straight-chain or branched. With regard to alcohol as such, plural kinds may be used as well. Among the above, it is preferred to use ethanol. Amount of the water-soluble organic solvent contained in the washing solution is preferably 20 to 100% by mass and, more preferably, it is 40 to 80% by weight.

On the other hand, it is preferred that a water-soluble salt contained in the washing solution is a salt of a halide and a chloride is particularly preferred. Moreover, it is preferred that the water-soluble salt is univalent or divalent cation and alkaline metal salt and alkaline earth metal salt are particularly preferred. Among them, sodium salt and potassium salt are preferred and sodium salt is most preferred.

When the water-soluble salt is contained in the washing solution, it is preferred that its concentration is 10 mmol/L or more. Although there is no limitation for its upper limit so far as solubility of impurities is not deteriorated, 1 mol/L or less is preferred and 0.1 mol/L or less is more preferred. It is still more preferred when the water-soluble salt is sodium chloride and it is particularly preferred that 20 mmol/L or more sodium chloride is contained.

With regard to buffer and surface-active agent, those which are already mentioned under the heading of [Pretreatment solution] may be exemplified. Among them, it is preferred that a washing solution contains ethanol, Tris and Triton-X100. Preferred concentrations of Tris and Triton-X100 are 10 to 100 mmol/L and 0.1 to 10% by mass, respectively.

It is preferred that a washing solution does not contain a chaotropic substance. As a result thereof, it is possible to reduce the possibility of contamination of a chaotropic substance in a recovering step after the washing step. When a chaotropic substance is contaminated in the recovering step, enzymatic reaction such as PCR (polymerase chain reaction) is often inhibited and, therefore, when enzymatic reaction, etc. thereafter are taken into consideration, it is ideal that the washing solution does not contain a chaotropic substance. In addition, chaotropic substance is corrosive and toxic and, therefore, the fact that use of a chaotropic substance is unnecessary is very advantageous for persons conducting experiments in view of safety of test operations. Here, a chaotropic substance is the above-mentioned urea, guanidine salt, sodium isocyanate, sodium iodide, potassium iodide, etc.

During the washing step in the conventional method for isolating and purifying a nucleic acid, wetting of the washing solution to a container used for the method for isolating and purifying a nucleic acid is high and, therefore, the washing solution often remains in the container and, in a recovering step after the washing step, that is a cause for reduction in purity of the isolated nucleic acid due to mixing of a washing solution, for reduction in reactivity in case the next step (such as a PCR) is conducted after the recovering step, etc. Accordingly, when adsorption and desorption of nucleic acid are carried out using a container, it is desirable that the residual solution of the washing solution does not remain in the container so that a solution used for adsorption and washing, especially a washing solution, do not affect the recovering step and the steps after the recovering step.

Therefore, it is preferred to make the surface tension of the washing solution less than 0.035 $J/m^2$ so that contamination of a washing solution in a washing step into an elution solution in a recovering step is prevented and remaining of the washing solution in the container is made minimum. When the surface tension is low, wetting of the container with the washing solution is enhanced and amount of the remained solution is able to be suppressed whereby that is preferred.

Although it is possible to enhance a washing efficiency when the proportion of water in a washing solution is increased, surface tension of the washing solution rises whereby the amount of the remained solution increases. When surface tension of the washing solution is 0.035 $J/m^2$ or more, amount the remained solution can be suppressed by enhancing the water repellency of the container. When water repellency of the container is enhanced, liquid drops are formed and, when the liquid drops flow down, amount of the remained solution is able to be suppressed. With regard to a method for enhancing the water repellency, there are means such as that a water-repellent such as silicon is coated on the surface of the container and that a water-repellant such as silicon is kneaded during the molding of a container although they are non-limitative.

Amount of the washing solution in a washing step is preferably 2 $\mu l/mm^2$ or more. When amount of the washing solution is too much, washing effect is improved. However, when it is made not more than 200 $\mu l/mm^2$, operability is able to be maintained and flowing-out of the sample is able to be suppressed whereby that is preferred.

It is preferred that a flow rate of a washing solution in contacting to a solid phase in a washing step is 2 to 1,500 $\mu L/sec$ per unit area or 1 $cm^2$ of the solid phase and, more preferably, it is 5 to 700 $\mu L/sec$. When much time is used by lowering the flow rate, washing is able to be well conducted to such an extent. However, when the above-mentioned range is used, an operation of isolating and purifying a nucleic acid is made fast without lowering the detergency efficiency whereby that is preferred.

In the washing step, it is preferred that liquid temperature of the washing solution is 4 to 70° C. It is more preferred that liquid temperature of the washing solution is room temperature. It is also possible that, in the washing step, mechanical oscillation and stirring by ultrasonic wave are applied to a container used for a method for isolating and purifying a nucleic acid together with the washing step. Alternatively, it is also possible to wash by conducting a centrifugal separation.

<Recovering Step (Desorbing Step)>

After the washing step, the solid after washing is contacted to an elution solution which is a solution being able to desorb nucleic acid adsorbed with the solid phase. Since the solution after contacting to the solid phase (hereinafter, this is sometimes referred to as a solution after purification) contains the aimed nucleic acid, it is provided to amplification of nucleic acid in the succeeding step such as by PCR (polymerase chain reaction).

When volume of the elution solution to volume of the sample solution containing nucleic acid prepared from the sample is adjusted, it is now possible to conduct desorption of nucleic acid. Volume of the used elution solution containing isolated and purified nucleic acid (volume of the solution after purification) depends upon the amount of the sample which is used in isolation and purification of the nucleic acid at that time. Generally and commonly used amount of the elution solution after purification is from several tens to several hundred $\mu l$ but, when amount of the sample is very small or, conversely, when large amount of nucleic acid is to be isolated and purified, amount of the elution solution after purification may be changed within a range of from 1 $\mu l$ to several tens $\mu l$.

With regard to an elution solution, it is possible to use pure distilled water, Tris/EDTA buffer, etc. It is preferred that pH of the elution solution is 2 to 11. More preferably, it is 5 to 9. In addition, ionic strength and salt concentration particularly affect the elution of adsorbed nucleic acid. It is preferred that the elution solution is a solution where a salt concentration is 0.5 mol/L or less. It is preferred that ionic strength of the elution solution is 500 ml/L or less. More preferably, the ionic strength is 290 mmol/L or less and, still more preferably, the ionic strength is 90 mmol/L or less. As a result thereof, recovering rate of nucleic acid is improved and much more nucleic acid is able to be recovered.

When volume of the elution solution is made small as compared with volume of the initial sample solution containing nucleic acid, an elution solution containing concentrated nucleic acid is able to be obtained. Preferably, the ratio of (volume of elution solution):(volume of sample solution) is from 1:100 to 99:100 and, more preferably, the ratio of (volume of elution solution):(volume of sample solution) is from 1:10 to 9:10. As a result thereof, nucleic acid is able to be easily concentrated without an operation for concentration in a step after isolation and purification of nucleic acid. By those methods, there are provided methods for preparing a nucleic acid solution in which nucleic acid is concentrated as compared with the sample whereby that is preferred.

There is no limitation how many times the elution solution is infused and that may be one time or plural times. When nucleic acid is isolated and purified quickly and easily, that is usually conducted by one recovery but, when a large amount of nucleic acid is recovered, etc., the elution solution may be infused for plural times.

It is also possible that, in the recovering step, a stabilizer for prevention of decomposition of recovered nucleic acid is added to the elution solution for nucleic acid. With regard to the stabilizer, it is possible to add antibacterial agent, antifungal agent and suppressor for decomposition of nucleic acid. With regard to a suppressor for decomposition of nucleic acid, an inhibitor for nuclease may be exemplified and, to be more specific, EDTA and the like may be exemplified. Further, it is also possible as another embodiment to previously add a stabilizer to a container for recovery.

<Cartridge for Isolating and Purifying a Nucleic Acid>

In the method for isolating and purifying a nucleic acid according to the present invention, adsorption and desorption of nucleic acid is able to be carried out using a cartridge for isolating and purifying a nucleic acid where the above-mentioned solid phase is received in a container preferably having at least two openings.

There is no particular limitation for a material of the container and anything may be used so far as it is able to receive a solid phase and is able to install at least two openings. In view of easiness in the manufacture, plastic is preferred. It is preferred to use a transparent or semitransparent plastic such as polystyrene, polymethacrylate, polyethylene, polypropylene, polyester, Nylon and polycarbonate.

There is also no particular limitation for the shape of a solid phase received in the above-mentioned container and that may be any shape such as circular, square, rectangular and elliptic and, in the case of membrane, it may be tubular, rolled or beady where an organic macromolecule having hydroxyl group on the surface is coated. In view of a manufacturing aptitude, a shape having high symmetry such as circle, square, cylinder or roll and beads are preferred.

It is preferred that inner volume of a container is determined by the volume of a sample solution to be treated and, usually, it is expressed in terms of volume of a solid phase to be received therein. Thus, it is preferred to be in such a size that one to about six sheet(s) of solid phase where thickness is about 1 mm or less (such as about 50 to 500 μm) and diameter is about 2 mm to 20 mm is/are received.

It is preferred that the end of the side contacting the container of the solid phase is closely adhered to the inner wall surface of the container to such an extent that a sample solution, etc. do not pass.

It is preferred that a side to an opening used as an inlet for a sample solution, etc. (an opening side from the solid phase in the container) from the solid phase of the container having at least two openings is made in such a structure that it not closely adhered to the inner wall of the container but space is placed there so that a sample solution, etc. is diffused to whole surface of the solid phase as uniform as possible.

<Unit for Isolating and Purifying a Nucleic Acid>

More preferably, a method for isolating and purifying a nucleic acid according to the present invention uses a unit for isolating and purifying a nucleic acid containing (a) a solid phase, (b) a container having at least two openings which receives the above solid phase and (c) an apparatus for generating the pressure difference connected to one of the openings of the above container.

In the unit for isolating and purifying a nucleic acid, (a) and (b) are the same as those in the cartridge for separation and purification mentioned already and, hereinafter, the corresponding part in a unit for isolating and purifying a nucleic acid may also be mentioned as a cartridge for isolating and purifying a nucleic acid. The unit for isolating and purifying a nucleic acid will now be illustrated as follows.

The container may be in such a state that it has a receiving part for a solid phase, that a solid phase is able to be received in the receiving part, that the solid phase does not come out of the receiving part upon suction and discharge of the sample solution, etc. and that an apparatus for generating the pressure difference is able to be connected to an opening. For such a purpose, it is preferred that the container is initially divided into two parts and, after receiving the solid phase, they are able to be united. In addition, it is possible to place meshes prepared by a material which does not pollute nucleic acid on an beneath the solid phase, whereby coming-out of the solid phase from the receiving part is able to be avoided, whereupon that is preferred.

The container is usually prepared in a manner of being divided into a body receiving the solid phase and a cover where at least one opening is installed in each of them. The opening is used as an inlet and outlet for a sample solution containing nucleic acid, a washing solution and an elution solution (hereinafter, they will be referred to as "sample solution, etc.") and is connected to an apparatus for generation of pressure difference by which the inner area of the container is able to be made into a state of reduced or high pressure. Although there is no particular limitation for the shape of the body, it is preferred that its cross section is made circular whereby the manufacture is easy and the sample solution, etc. are apt to be diffused on the whole surface of the solid state. It is also preferred to make the cross section square so that no offcut of the solid phase is generated.

It is necessary that the above cover is connected to the body in such a manner that the inner area of the container is made into a state of reduced or high pressure by means of the apparatus for generating the pressure difference and, when once such a state is achieved, the connecting method is able to be freely selected. Examples thereof are use of an adhesive, stuffing, inserting, screwing and fusion by means of ultrasonic heating.

Examples of an apparatus for generation of pressure difference are injection syringe, pipetter and pump which is able to suck and compress such as peristaltic pump. Among them, injection syringe and pump are suitable for manual operation and automatic operation, respectively. Pipetter has an advantage that an operation by one hand is easily carried out. Preferably, the apparatus for generation of pressure difference is connected in a detachable manner to one opening of the above-mentioned container.

When three or more openings are installed in a container, it goes without saying that an excessive opening is to be temporarily closed so that suction and discharge as a result of an operation for giving reducing and high pressure are made possible.

The first embodiment of the method for isolating and purifying a nucleic acid according to the present invention may include the following steps. They are:

(1a) a step where a sample solution containing nucleic acid is prepared using a sample and one of openings of a container housing a solid phase and having at least two openings is inserted into the sample solution, (1b) a step where the sample solution containing nucleic acid is sucked when the inner area of the container is made in a state of reduced pressure using an apparatus for generation of pressure difference connected to another opening of the container housing a solid phase and having at least two openings and then it is contacted to the solid phase, (1c) a step where the inner area of the container is made into a pressurized state using an apparatus for generation of pressure difference connected to the above-mentioned another opening, and the sucked sample solution containing nucleic acid is discharged outside the container, (1d) a step where the above-mentioned one opening is inserted into a washing solution, (1e) a step where the washing solution is sucked when the inner area of the container is made in a state of reduced pressure using an apparatus for generation of pressure difference connected to the above-mentioned another opening and then it is contacted to the solid phase, (1f) a step where the inner area of the container is made into a pressurized state using an apparatus for generation of pressure difference connected to the above-mentioned another opening and the sucked washing solution is discharged outside the container, (1g) a step where the above-mentioned one opening is inserted into an elution solution, (1h) a step where the elution solution is sucked when the inner area of the container is made in a state of reduced pressure using an apparatus for generation of pressure difference connected to the above-mentioned another opening and then it is contacted to the solid phase and (1i) a step where the inner area of the container is made into a pressurized state using an apparatus for generation of pressure difference connected to the above-mentioned another opening and the sucked elution solution is discharged outside the container.

In the steps of (1b), (1e) and (1h), it is preferred that a solution is sucked in such an amount that it contacts to nearly the whole area of the solid phase. However, the apparatus is polluted when it is sucked into an apparatus for generating the pressure difference and, therefore, that is appropriately adjusted. After an appropriate amount of a solution is sucked, the inner area of the container is pressurized using the apparatus for generating the pressure difference and the sucked solution is discharged. It is not necessary to make time until such an operation but a discharge may be conducted immediately after the suction.

As one of the preferred embodiments of a unit for isolating and purifying a nucleic acid for conducting the above-mentioned first embodiment, an apparatus for isolating and purifying a nucleic acid mentioned in Japanese Patent Laid-Open No. 2004/180,637 may be exemplified.

In a unit for isolating and purifying a nucleic acid for conducting the first embodiment, it is preferred to install a material where pore is formed near its center on a solid phase encountering the opening connected to the apparatus for generation of the pressure difference. The material has an effect of pressing down the solid phase and also discharging the sample solution, etc. efficiently and it is preferred in a shape of having a slope such as funnel or cup so that the solution is accumulated to the central pore. Size of the pore, angle of the slope and thickness of the material are able to be appropriately determined by persons skilled in the art by taking the amount of the sample solution, etc. to be treated, the size of the container receiving the solid phase and so on into consideration. It is preferred that, between the material and the opening, a space for storing the overflowed sample solution, etc. and for prevention of sucking into the apparatus for generating the pressure difference is installed. Size of the space is also able to be appropriately selected by persons skilled in the art. Incidentally, for a purpose of efficient collection of nucleic acid, it is preferred to suck a sample solution containing nucleic acid in an amount which is not less than that whereinto the entire solid phase is dipped.

In addition, for such a purpose that concentration of the sample solution, etc. only to the part immediately beneath the sucking opening so that the sample solution, etc. are able to pass through the solid phase relatively uniformly, it is preferred that a space is installed between the solid phase and the material as well. For such a purpose, it is preferred to install plural projections from the material to the solid phase. Although size and numbers of the projections may be appropriately selected by persons skilled in the art, it is preferred that they are as large as possible within such an extent that the opening area of the solid phase is able to be kept as big as possible while the space is retained.

The second embodiment of the method for isolating and purifying a nucleic acid according to the present invention may include the following steps:

(2a) a step of preparing a sample solution containing nucleic acid from a sample and infusing the sample solution containing nucleic acid into one of the openings of the container housing the solid phase, the container having at least two openings;

(2b) a step of making the inner area of the container into a pressurized state by using the apparatus for generating the pressure difference being connected to the one of the openings of the container and contacting the infused sample solution containing nucleic acid to the solid phase by discharging the sample solution from another opening of the container to adsorb nucleic acid onto the solid phase;

(2c) a step of detaching the apparatus for generating the pressure difference from the one opening of the container and infusing a washing solution into the one opening of the container;

(2d) a step of making the inner area of the container into a pressurized state by using the apparatus for generating the pressure difference being connected to one of the openings of the container and discharging the infused washing solution from another opening of the container to contact the washing solution to the solid phase to wash the solid phase;

(2e) a step of detaching the apparatus for generating the pressure difference from the one opening of the container and infusing an elution solution into the one opening of the container; and (2f) a step of making the inner area of the container into a pressurized state by using the apparatus for generating the pressure difference being connected to the one of the openings of the container and discharging the infused elution solution from another opening of the container to desorb the adsorbed nucleic acid from the solid phase and discharge nucleic acid outside the container.

In the above-mentioned steps, there is no particular limitation for adding the sample solution to a container although it is preferred to use experimental tools such as pipette and syringe. When such tools are nuclease-free or pyrogen-free, that is more preferred.

There is no particular limitation for a method of mixing the sample. For example, when a stirring device is used in the mixing, it is preferred to mix at 30 to 3,000 rpm for 1 second to 30 minutes. It is preferred that yield of the isolated and purified nucleic acid is able to be increased as a result thereof. In the case of a reversing mixing, it is preferred to conduct the mixing for 5 to 30 times. In the case of a pipetting operation, it is preferred to conduct the mixing for 10 to 50 times.

It is also possible to selectively separate and purify RNA only from a nucleic acid mixture containing DNA and RNA when a step of washing the solid phase using a washing solution is conducted after a DNase solution is contacted to the solid phase (2d') before the above-mentioned step (2e). There is no particular limitation for the DNase and any of known DNases may be used.

Reagents to be used for the above-mentioned method for isolating and purifying a nucleic acid may be made into a kit. A reagent kit contains the above-mentioned antifoaming agent, pretreatment solution, washing solution and elution solution.

As an example of embodiments for conducting the method for isolating and purifying a nucleic acid according to the present invention, it is also possible to use an automated apparatus.

Hereinafter, there is shown an example of an apparatus where a step of isolating and purifying a nucleic acid from a sample containing nucleic acid is automatically conducted using a solid phase, a container receiving the solid phase and having at least two openings and an apparatus for generation of pressure difference although the automated apparatus is not limited thereto.

With regard to an automated apparatus, it is an apparatus for isolating and purifying a nucleic acid in which a container (cartridge for isolating and purifying a nucleic acid) housing a solid phase which adsorbs nucleic acid and having at least two openings where a solution is able to pass through the inner area is used, a sample solution containing nucleic acid is infused into the cartridge for isolating and purifying a nucleic acid, nucleic acid in the sample solution is adsorbed with the solid phase by pressurizing, then a washing solution is dispensed to the cartridge for isolating and purifying a nucleic acid followed by pressurizing to remove the impurities, an elution solution is infused to the cartridge for isolating and purifying a nucleic acid and nucleic acid adsorbed with the solid phase is desorbed and recovered together with an elution solution. The apparatus for isolating and purifying a nucleic acid is characterized in that the apparatus is equipped with a loading mechanism which holds a waste solution container receiving the discharged solution of sample solution and washing solution and a recovering container receiving the elution solution of nucleic acid, a compressed air supplying mechanism which introduces pressurized air into the cartridge for isolating and purifying a nucleic acid and an dispensing mechanism which dispenses the washing solution and the elution solution into the cartridge for isolating and purifying a nucleic acid.

With regard to the above loading mechanism, it is suitable to be equipped with a stand which is installed in the body of the apparatus, a cartridge holder which holds the cartridge for isolating and purifying a nucleic acid being supported by the stand and being able to move up and down and a container holder which holds the above waste solution container and elution solution container in an exchangeable manner in terms of their positions to the cartridge for isolating and purifying a nucleic acid.

With regard to the above pressurized air supplying mechanism, it is suitable to be equipped with an air nozzle which spouts the pressurized air from the lower end, a pressurizing head which holds the above air nozzle and ascends and moves the air nozzle against the cartridge for isolating and purifying a nucleic acid being held by the holder and a positioning means which positions the cartridge for isolating and purifying a nucleic acid in the rack in the loading mechanism.

With regard to the above dispensing mechanism, it is suitable to be equipped with a nozzle for dispensing the elution solution which dispenses the elution solution, a nozzle moving stand which holds the dispensing nozzle for washing solution and the dispensing nozzle for elution solution and is able to successively move on the cartridge for isolating and purifying a nucleic acid held by the cartridge holder in the above loading mechanism, a washing solution supplying pump which sucks a washing solution from a washing solution pump receiving the washing solution and supplied to the washing solution dispensing nozzle and an elution solution supplying pump which sucks an elution solution from an elution solution bottle receiving the elution solution and supplied to the elution solution dispensing nozzle.

According to the automatic apparatus as mentioned above, it is now possible to compactly constitute a mechanism which is equipped with a loading mechanism holding cartridge for isolating and purifying a nucleic acid, waste solution container and recovering container, a pressurized air supplying mechanism introducing pressurized air into the cartridge for isolating and purifying a nucleic acid and an infusion mechanism infusing the washing solution and the elution solution into the cartridge for isolating and purifying a nucleic acid and which infuses and pressurizes a sample solution containing nucleic acid into the cartridge for isolating and purifying a nucleic acid equipped with a solid phase material so that nucleic acid is adsorbed with the solid phase material, the washing solution is infused to wash and discharge the impurities and the elution solution is infused so that nucleic acid adsorbed with the solid phase membrane material is isolated and recovered automatically whereby nucleic acid in the sample solution is able to be automatically isolated and purified within a short time and with a high efficiency.

Further, when the above loading mechanism is constituted by being equipped with a stand, a holder which holds the cartridge for isolating and purifying a nucleic acid and is able to move up and down and a container holder which holds the waste solution container and the recovering container in an exchangeable manner, it is now possible that setting of the cartridge for isolating and purifying a nucleic acid and both of the containers and exchange of the waste solution container and the recovering container are easily carried out.

Furthermore, when the above pressurized air supplying mechanism is constituted by being equipped with an air nozzle, a pressurizing head which moves the air nozzle up and down and a positioning means which positions the cartridge for isolating and purifying a nucleic acid, it is now possible to supply the pressurized air by a simple mechanism.

Still further, when the above dispensing mechanism is constituted by being equipped with a washing solution dispensing nozzle, an elution solution dispensing nozzle, a nozzle moving stand which is able to successively move on the cartridge for isolating and purifying a nucleic acid, a washing solution supplying pump which sucks the washing solution from the washing solution bottle and supplies to the washing solution dispensing nozzle and an elution solution supplying pump which sucks the elution solution from the elution solution bottle and supplies to the elution solution dispensing nozzle, it is now possible to successively infuse the washing solution and the elution solution by a simple mechanism.

The present invention will now be further illustrated by way of the following Examples although the present invention is not limited thereto.

EXAMPLE 1

(1) Materials and Reagents

Using a unit for isolating and purifying a nucleic acid having a structure as shown in FIG. 1 to FIG. 6 of Japanese Patent Laid-Open No. 2004/180,637, reagent, washing solution and distilled water were successively infused from the second opening side and, for each operation, a piston material (plunger) is inserted and pushed. With regard to a solid phase for adsorption of nucleic acid, Fuji Microfilter FR 250 (manufactured by Fuji Photo Film) was used. Pretreatment solutions (Comparative Example and the present invention) and washing solution were prepared as follows.

| [Pretreatment solution (Comparative Example)] | |
|---|---|
| Guanidine hydrochloride (manufactured by Life Technology) | 382 g |
| Tris (manufactured by Life Technology) | 12.1 g |
| Triton-X 100 (manufactured by ICN) | 10 g |
| Distilled water | 1,000 ml |
| [Pretreatment solution (the Present Invention)] | |
| Guanidine hydrochloride (manufactured by Life Technology) | 382 g |
| Tris (manufactured by Life Technology) | 12.1 g |
| Triton-X 100 (manufactured by ICN) | 10 g |
| Acetylene glycol (manufactured by Air Products) | 10 g |
| Silicone oil (manufactured by GE Toshiba Silicone) | 2 g |
| Distilled water | 1,000 ml |
| [Washing solution] | |
| 10 mmol/L Tris-HCl | 65% ethanol |

(2) Operation for Isolating and Purifying a Nucleic Acid

To human whole blood sample (200 μl) were added 200 μl of the pretreatment solution of the present invention and 200 μl of protease K and incubation was conducted at 60° C. for 10 minutes. After the incubation, 200 μl of ethanol was added followed by stirring. After the stirring, the solution was infused into to a unit for isolating and purifying a nucleic acid where a structure thereof is shown in FIG. 1 to FIG. 6 of Japanese Patent Laid-Open No. 2004/180,637. After the infusion, a liquid was pushed out using a piston.

After that, 500 μl of a washing solution was infused and the liquid was pushed out using a piston to wash the unit and impurities on the adsorbed solid phase. Finally, 200 μl of distilled water was infused, the solution was pushed out using a piston and the solution was recovered as a DNA solution.

An operation of isolating and purifying a nucleic acid was conducted by the same manner as in the present invention except that the pretreatment solution for Comparative Example was used as a pretreatment solution.

(3) Quantification of Recovered Amount of Nucleic Acid

Yields of DNA purified by the operation of (2) and foam height (value where, upon discharging the sample solution, length of foams generated from the opening was measured) are shown in the following Table 1. According to the above-mentioned unit for isolating and purifying a nucleic acid, it is now possible to easily conduct an operation of isolating and purifying a nucleic acid and, from the result of Table 1, it was noted that, in the present invention, generated amount of foams was able to be suppressed.

TABLE 1

| Sample Nos. | DNA (μg) | Height of Foams |
|---|---|---|
| 1 (Present Invention) | 4.2 | 7 mm |
| 2 (Present Invention) | 3.6 | 5 mm |
| 3 (Present Invention) | 5.7 | 3 mm |
| 4 (Present Invention) | 6.3 | 5 mm |
| 5 (Present Invention) | 5.0 | 11 mm |
| 1 (Comparative Example | 4.4 | 32 mm |
| 2 (Comparative Example | 3.9 | 30 mm |
| 3 (Comparative Example | 4.2 | 24 mm |
| 4 (Comparative Example | 5.8 | 45 mm |
| 5 (Comparative Example | 6.3 | 60 mm |

EXAMPLE 2

(1) Preparation of Cartridge for Isolating and Purifying a Nucleic Acid

A container having inner diameter of 7 mm, having a part receiving a porous membrane which adsorbs nucleic acid as a solid phase and having at least two openings was prepared using a high-impact polystyrene.

(2) A porous membrane (pore size: 2.5 μm; diameter: 7 mm; thickness: 100 μm; degree of saponification: 95%) prepared by subjecting a porous membrane of triacetyl cellulose to saponification was used as a porous membrane which is able to adsorb nucleic acid and received in a part for receiving a porous membrane of a container having at least two openings prepared in the above (1).

(3) Preparation of pretreatment solution and washing solution

A pretreatment solution and a washing solution having the following formulations were prepared.

| (Pretreatment solution) | |
|---|---|
| β-Mercaptoethanol | 9 g |
| Guanidine hydrochloride (manufactured by Life Technology) | 382 g |
| Tris (manufactured by Life Technology) | 12.1 g |
| Triton-X 100 (manufactured by ICN) | 10 g |
| Acetylene glycol (manufactured by Air Products) | 10 g |
| Silicone oil (manufactured by GE Toshiba Silicone) | 2 g |
| Distilled water | added to make 1,000 ml |
| (Washing solution) | |
| 10 mM Tris-HCl | 30% ethanol |

(4) Operation for Isolating and Purifying a Nucleic Acid

An incubated solution of cancerous human bone marrow cells (HL 60) was prepared. The incubated solution (200 μl; cell numbers: $5 \times 10^5$) was infused into a container of a nuclease-free and pyrogen-free 1.5-mL microtube (Platinum Tube; manufactured by BM Kiki) using a dispensing pipette (Pipetman; manufactured by Gilson) equipped with a nuclease-free and pyrogen-free chip (Platinum Chip; manufactured by BM Kiki), 200 μl of the above-mentioned pretreating solution and 20 μl of a solution of Protease K (manufactured by Sigma) which is a protease were added thereto and mixed therewith by applying Vortex for 15 minutes and the mixture was incubated at 60° C. for 10 minutes. After incubation, 200 μl of ethanol was added followed by stirring. After stirring, it was infused into an opening of the cartridge for isolating and purifying a nucleic acid prepared in the above (2), then an apparatus for generation of pressure difference (tubing pump) was connected the opening, inner area of the cartridge for isolating and purifying a nucleic acid is made into a pressurized state (80 kPa) and the infused sample solution containing nucleic acid was passed through a porous membrane being able to adsorb nucleic acid and discharged form another opening of the cartridge for isolating and purifying a nucleic acid. After that, a washing solution was infused into the above opening of the above cartridge for isolating and purifying a nucleic acid, a tubing pump was connected to the opening, the inner area of the cartridge for isolating and purifying a nucleic acid was made into a pressurized state (80 kPa) and the infused washing solution was passed through a porous membrane being able to adsorb nucleic acid and discharged from another opening. After that, an elution solution was infused into the opening of the above cartridge for isolating and purifying a nucleic acid, the inner area of the cartridge for isolating and purifying a nucleic acid was made into a pressurized state (80 kPa) by connecting to the opening of the cartridge for isolating and purifying a nucleic acid and the infused elution solution was passed through a porous membrane being able to adsorb nucleic acid and discharged from another opening to recover the solution. Time required for the operation of isolating and purifying a nucleic acid (from infusion of the sample solution containing nucleic acid into the above cartridge for isolating and purifying a nucleic acid until recovering) was 2 minutes.

(5) Quantification of Recovered Amount of Nucleic Acid

Figure 1:
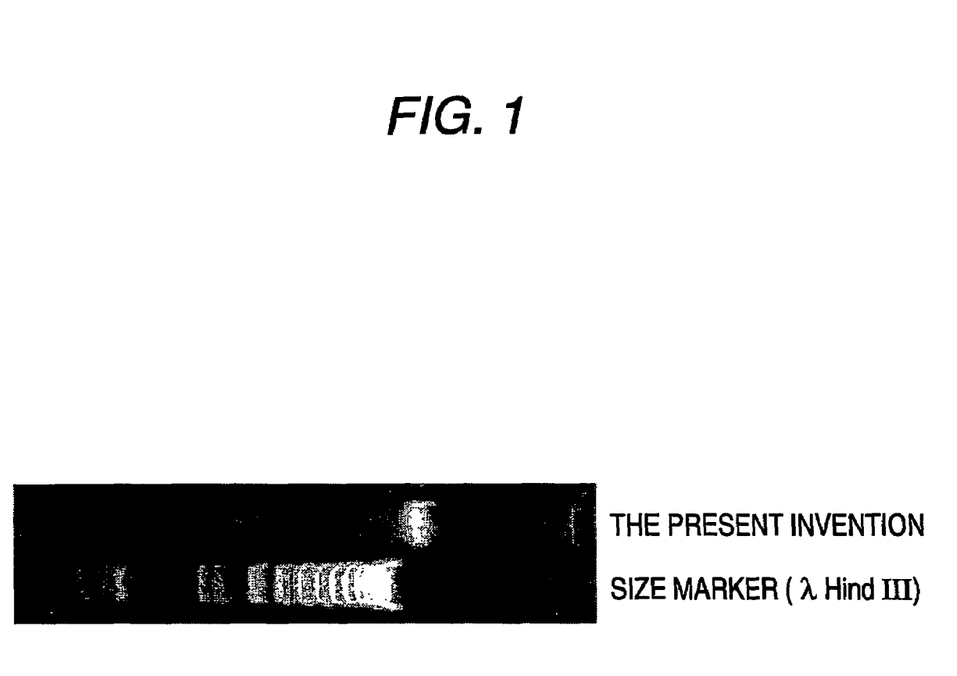
FIG. 1 is a photograph obtained by electrophoresis of molecular marker and nucleic acid isolated and purified by the method of the present invention.

The experiment of Example 1 was carried out. FIG. 1 shows the result of electrophoresis of nucleic acid purified from a sample solution containing nucleic acid according to the method of the present invention.

As will be apparent from the result of FIG. 1, it is understood that, when the method of the present invention is used, nucleic acid is able to be isolated and purified with a very high efficiency. Thus, the method of the present invention had excellent separation efficiency and good detergency efficiency and, therefore, nucleic acid was able to be prepared quickly and in a high yield within the above-mentioned time.

INDUSTRIAL APPLICABILITY

In accordance with the method of the present invention, generation of foams can be suppressed whereby it is now possible that nucleic acid of high purity is easily and efficiently isolated from a sample solution containing nucleic acid. It is also possible that, by the use of an apparatus for conducting the method for isolating and purifying a nucleic acid and a reagent kit to be used for the method for isolating and purifying a nucleic acid, generation of foams is suppressed and nucleic acid is recovered more easily and quickly.

The invention claimed is:

1. A method for isolating and purifying a nucleic acid, comprising the step of:
   (1) contacting a sample solution containing nucleic acid to a solid phase to adsorb the nucleic acid onto the solid phase;
   (2) contacting a washing solution to the solid phase to wash the solid phase in such a state that the nucleic acid is adsorbed; and
   (3) contacting an elution solution to the solid phase to desorb the nucleic acid,
   wherein the sample solution containing nucleic acid is prepared by further addition and mixing of a pretreatment solution containing an antifoaming agent and a surface-active agent,
   wherein the antifoaming agent is an alcohol-type antifoaming agent selected from at least one of the group consisting of: acetylene glycol, heptanol, and ethylhexanol,
   wherein the sample solution containing nucleic acid is prepared by further addition of a water-soluble organic solvent,
   wherein the solid phase is a porous membrane having an average pore diameter of 0.1 to 10.0 μm.

2. The method for isolating and purifying a nucleic acid according to claim 1, wherein the sample solution containing nucleic acid is prepared by further addition and mixing of a pretreatment solution containing at least one selected from the group consisting of a nucleic acid stabilizer, a chaotropic salt, buffer and a protease.

3. The method for isolating and purifying a nucleic acid according to claim 1, wherein the antifoaming agent further comprises a silicon type antifoaming agent.

4. The method for isolating and purifying a nucleic acid according to claim 2, wherein the pretreatment solution contains the nucleic acid stabilizer in a concentration of 0.1 to 20% by mass.

5. The method for isolating and purifying a nucleic acid according to claim 2, wherein the nucleic acid stabilizer is a reducing agent.

6. The method for isolating and purifying a nucleic acid according to claim 5, wherein the reducing agent is a mercapto compound.

7. The method for isolating and purifying a nucleic acid according to claim 2, wherein the nucleic acid stabilizer is a chelating agent.

8. The method for isolating and purifying a nucleic acid according to claim 2, wherein the chaotropic agent is a guanidium salt.

9. The method for isolating and purifying a nucleic acid according to claim 1, wherein the water-soluble organic solvent contains at least one selected from the group consisting of methanol, ethanol, propanol and butanol.

10. The method for isolating and purifying a nucleic acid according to claim 1, wherein the solid phase is a solid phase containing silica or a derivative thereof, diatomaceous earth or alumina.

11. The method for isolating and purifying a nucleic acid according to claim 1, wherein the solid phase is a solid phase containing an organic macromolecule.

12. The method for isolating and purifying a nucleic acid according to claim 11, wherein the organic macromolecule is an organic macromolecule having a polysaccharide structure.

13. The method for isolating and purifying a nucleic acid according to claim 11, wherein the organic macromolecule is acetylcellulose.

14. The method for isolating and purifying a nucleic acid according to claim 11, wherein the organic macromolecule is an organic macromolecule where acetylcellulose or a mixture of acetylcelluloses having different acetyl values is subjected to a saponification treatment.

15. The method for isolating and purifying a nucleic acid according to claim 14, wherein degree of saponification of the organic macromolecule prepared by a saponification treatment of the mixture of acetylcelluloses having different acetyl values is 5% or more.

16. The method for isolating and purifying a nucleic acid according to claim 14, wherein degree of saponification of the organic macromolecule prepared by a saponification treatment of the mixture of acetylcelluloses having different acetyl values is 10% or more.

17. The method for isolating and purifying a nucleic acid according to claim 11, wherein the organic macromolecule is a regenerated cellulose.

18. The method according to claim 10, wherein the porous membrane is a porous membrane, in which the front and back sides are asymmetric.

19. The method according to claim 10, wherein the porous membrane is a porous membrane having a thickness of 10 to 500 μm.

20. The method according to claim 10, wherein the solid phase is coated magnetic beads.

21. The method for isolating and purifying a nucleic acid according to claim 1, wherein the adsorption and desorption of nucleic acid are carried out using a cartridge for isolating and purifying a nucleic acid, which houses the solid phase in a container having at least two openings.

22. The method for isolating and purifying a nucleic acid according to claim 1, wherein the adsorption and desorption of nucleic acid are carried out using a unit for isolating and purifying a nucleic acid, which has:

(a) the solid phase;
(b) a container having at least two openings, which houses the solid phase; and
(c) an apparatus for generating the pressure difference, which is connected to one of the openings of the container.

23. The method for isolating and purifying a nucleic acid according to claim 22, wherein the apparatus for generating the pressure difference is an apparatus for pressurization.

24. The method for isolating and purifying a nucleic acid according to claim 22, wherein the apparatus for generating the pressure difference is an apparatus for pressure reduction.

25. The method for isolating and purifying a nucleic acid according to claim 22, wherein the apparatus for generating the pressure difference is connected to one of the openings of the container in a freely detachable manner.

26. The method for isolating and purifying a nucleic acid according to claim 22, which comprises the step of:

(2a) preparing a sample solution containing nucleic acid from a sample and infusing the sample solution containing nucleic acid into one of the openings of the container housing the solid phase, the container having at least two openings;
(2b) making the inner area of the container into a pressurized state by using the apparatus for generating the pressure difference being connected to the one of the openings of the container and contacting the infused sample solution containing nucleic acid to the solid phase by discharging the sample solution from another opening of the container to adsorb nucleic acid onto the solid phase;
(2c) detaching the apparatus for generating the pressure difference from the one opening of the container and infusing a washing solution into the one opening of the container;
(2d) making the inner area of the container into a pressurized state by using the apparatus for generating the pressure difference being connected to one of the openings of the container and discharging the infused washing solution from another opening of the container to contact the washing solution to the solid phase to wash the solid phase;
(2e) detaching the apparatus for generating the pressure difference from the one opening of the container and infusing an elution solution into the one opening of the container; and
(2f) making the inner area of the container into a pressurized state by using the apparatus for generating the pressure difference being connected to the one of the openings of the container and discharging the infused elution solution from another opening of the container to desorb the adsorbed nucleic acid from the solid phase and discharge nucleic acid outside the container.

27. The method for isolating and purifying a nucleic acid according to claim 26, which comprises, before the step of (2e), (2d') contacting a solution of DNase to the solid phase and then washing the solid phase with the washing solution.

28. The method for isolating and purifying a nucleic acid according to claim 1, wherein the washing solution is a solution containing 20 to 100% by mass of methanol, ethanol, isopropanol or n-propanol.

29. The method for isolating and purifying a nucleic acid according to claim 1, wherein the elution solution is a solution having a salt concentration of not more the 0.5 mol/L.

* * * * *